United States Patent
Randolph et al.

(10) Patent No.: US 8,329,603 B2
(45) Date of Patent: Dec. 11, 2012

(54) ISOPARAFFIN-OLEFIN ALKYLATION

(75) Inventors: Bruce B. Randolph, Bartlesville, OK (US); Marvin M. Johnson, Bartlesville, OK (US); Glenn W. Dodwell, Bartlesville, OK (US)

(73) Assignee: UOP LLC, Des Plaines, IL (US)

( * ) Notice: Subject to any disclaimer, the term of this patent is extended or adjusted under 35 U.S.C. 154(b) by 589 days.

(21) Appl. No.: 10/663,416

(22) Filed: Sep. 16, 2003

(65) Prior Publication Data

US 2005/0059848 A1 Mar. 17, 2005

(51) Int. Cl.
*C03C 3/19* (2006.01)

(52) U.S. Cl. .......................................... 501/47

(58) Field of Classification Search ............... 502/150, 502/104; 526/127; 556/2, 6, 13; 501/47
See application file for complete search history.

(56) References Cited

U.S. PATENT DOCUMENTS

| | | | |
|---|---|---|---|
| 2,258,368 A * | 10/1941 | Stevens et al. ................ | 585/515 |
| 5,659,105 A | 8/1997 | Clerici et al. | |
| 5,663,474 A | 9/1997 | Pham et al. | |
| 5,714,611 A * | 2/1998 | Aumuller ..................... | 546/188 |
| 5,726,285 A * | 3/1998 | Aumuller et al. ............ | 528/422 |
| 5,792,869 A | 8/1998 | Murakami et al. ............ | 544/390 |
| 5,849,965 A | 12/1998 | Mehlberg et al. | |
| 5,877,383 A | 3/1999 | Hommeltoft et al. | |
| 5,892,124 A | 4/1999 | Olivier et al. ................. | 568/324 |
| 5,914,360 A * | 6/1999 | Aumuller ..................... | 524/102 |
| 6,025,529 A | 2/2000 | Bahrmann .................... | 568/454 |
| 6,107,230 A | 8/2000 | McDaniel et al. ............ | 502/104 |
| 6,165,929 A | 12/2000 | McDaniel et al. ............ | 502/117 |
| 6,177,058 B1 | 1/2001 | Singh et al. | |
| 6,395,666 B1 | 5/2002 | McDaniel et al. ............ | 502/87 |
| 6,465,391 B1 | 10/2002 | Cheung et al. ............... | 502/330 |
| 6,576,583 B1 * | 6/2003 | McDaniel et al. ............ | 502/104 |
| 2001/0024755 A1 * | 9/2001 | Bahar et al. .................. | 429/247 |
| 2004/0143078 A1 | 7/2004 | McDaniel et al. | |

FOREIGN PATENT DOCUMENTS

EP 0 889 848 B1 8/2001
WO WO 01/81436 A1 11/2001

OTHER PUBLICATIONS

Copending U.S. Appl. No. 10/350,716.*
Copending U.S. Appl. No. 10/357,212, filed 2003.
Copending U.S. Appl. No. 10/441,153, filed 2003.
Copending U.S. Appl. No. 10/445,379, filed 2003.

* cited by examiner

*Primary Examiner* — James McDonough
(74) *Attorney, Agent, or Firm* — James C Paschall

(57) ABSTRACT

A composition comprising a base component and a polymer, and a method of making said composition, are disclosed. The composition thereby obtained is then used as a catalyst for isoparaffin-olefin alkylation.

8 Claims, No Drawings

ISOPARAFFIN-OLEFIN ALKYLATION

The present invention relates to a hydrocarbon conversion process and a catalyst composition utilized in said hydrocarbon conversion process. More particularly, the invention relates to an improved alkylation process for the production of an alkylate product by contacting hydrocarbons with a novel composition.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling said mixture to separate the catalyst from the hydrocarbons, and further separating the hydrocarbons, for example, by fractionation, to recover the alkylation reaction product. Normally, the alkylation reaction product is referred to as "alkylate", and preferably contains hydrocarbons having to 7-9 carbon atoms. In order to have the highest quality gasoline blending stock, it is preferred that hydrocarbons formed in the alkylation process be highly branched.

One of the more desirable alkylation catalysts is hydrofluoric acid (HF), however, the use of hydrofluoric acid as an alkylation catalyst has certain drawbacks. One problem with the use of hydrofluoric acid as an alkylation catalyst is that it is corrosive and it is toxic to human beings. The toxicity of hydrofluoric acid to human beings is further complicated by the fact that anhydrous hydrogen fluoride is typically a gas at normal atmospheric conditions of one atmosphere of pressure and 70° F. It is possible for the vapor pressure of hydrofluoric acid at standard atmospheric conditions to pose an inhalation risk if it is inadvertently exposed to the atmosphere. Although the safety record associated with most HF based alkylation units is very good, the potential exists for inadvertent release of HF into the atmosphere.

Due to the vapor pressure and corrosion associated with hydrofluoric acid, it would be beneficial to have an alkylation process using a catalyst composition, which would be an alternative to hydrofluoric acid. One possible alternative is the use of different liquid acids. However, other liquid acids can present corrosion and toxicity problems as well and tend to suffer rapid deactivation. This also requires the catalyst to be transported around a reactor/regenerator loop. Therefore, it would be desirable to have an alkylation catalyst composition that does not undergo rapid deactivation.

SUMMARY OF THE INVENTION

It is, therefore, an object of this invention to provide a novel alkylation catalyst composition having the desirable property of yielding a high quality alkylate when utilized in the alkylation of olefins with paraffins, but which does not undergo rapid deactivation.

Another object of this invention is to provide a novel method to make a novel alkylation catalyst composition.

A further object of this invention is to provide a process for the alkylation of olefins with paraffins in the presence of an alkylation catalyst which produces an alkylate product.

Thus, the process of the present invention relates to the alkylation of a hydrocarbon mixture comprising olefins and paraffins with a catalyst composition comprising the components of an acid and a polymer.

Other objects and advantages of the invention will be apparent from the foregoing detailed description of the invention and the appended claims.

DETAILED DESCRIPTION OF THE INVENTION

The novel composition of the present invention is suitable for use as an alkylation catalyst and can comprise, consist of, or consist essentially of, an acid component and a polymer.

The acid component of the composition is selected from the group consisting of 1) a sulfuric acid, 2) a fluorosulfonic acid, 3) a perhaloalkylsulfonic acid, 4) an ionic liquid, 5) mixtures of Bronsted acids and Lewis acids, and 6) combinations of any two or more thereof. Preferably, the acid component is a perhaloalkylsulfonic acid. Most preferably, the acid component is trifluoromethanesulfonic acid.

The ionic liquid comprises, consists of, or consists essentially of a cation and an anion. The cation is preferably selected from the group consisting of ions defined by the formulas:

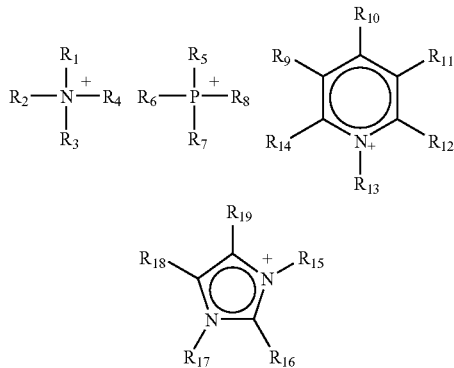

and combinations of any two or more thereof, wherein:
$R_1$, $R_2$, $R_3$, $R_5$, $R_6$, and $R_7$ are selected from saturated and unsaturated hydrocarbons containing from 1 to 7 carbon atoms per molecule; $R_4$, $R_8$, $R_9$, $R_{10}$, $R_{11}$, $R_{12}$, $R_{13}$, $R_{14}$, $R_{15}$, $R_{16}$, $R_{17}$, $R_{18}$ and $R_{19}$ are selected from saturated and unsaturated hydrocarbons containing from 1 to 7 carbon atoms per molecule and hydrogen.

The anion is selected from the group consisting of halides of: Group IIIA metals, copper, zinc, iron, phosphorus and combinations thereof.

Preferably, the mixtures of Bronsted acids and Lewis acids comprise, consist of, or consist essentially of, a Bronsted acid selected from the group consisting of hydrofluoric acid, sulfuric acid, trifluoromethanesulfonic acid, and combinations of any two or more thereof and any suitable Lewis acid, including, but not limited to, halides of Group IIIA metals such as $BF_3$, $AlCl_3$, $GaCl_3$, and other metal halides such as $TiF_4$.

Preferably, the polymer present in the inventive composition is a polyacrylate of the general formula [—$CH_2$—$CH(CO_2R)$—$_n$] wherein R is a Group IA element. Preferably the element is hydrogen. One important function of the presence of the polymer, preferably a polyacrylate, is to hold the acid component in place to a much greater degree than with other supports.

The acid component is generally present in the composition in a range of from about 5 weight-% to about 90 weight-% based on the total weight of the composition. Preferably, the acid component is present in the composition in the range of from about 30 weight-% to about 85 weight-% based on the total weight of the composition, and most preferably, the acid component is present in the composition in the range of from 50 weight-% to 80 weight-% based on the total weight of the composition.

According to the second embodiment of the present invention, a method for making a composition is disclosed. This method comprises, consists of, or consists essentially of admixing a polymer and an acid component selected from the group consisting of 1) a sulfuric acid, 2) a fluorosulfonic acid, 3) a perhaloalkylsulfonic acid, 4) an ionic liquid, 5) mixtures of Bronsted acids and Lewis acids, and 6) combinations of any two or more thereof, to form a mixture thereof. The term "admixing," as used herein, denotes mixing components in any order and/or any combination or sub-combination.

The description for the ionic liquid and the Bronsted acid/Lewis acid mixtures in the second embodiment are the same as in the first embodiment.

Preferably, the acid component is trifluoromethanesulfonic acid.

Preferably, the polymer is a polyacrylate having a formula of $[-CH_2-CH(CO_2R)-]_n$ where R is a Group IA element, preferably hydrogen.

The weight percents of the acid component and polymer in the first embodiment also apply to the second embodiment.

The acid component is added to the polymer at a rate so that the mixture does not swell too quickly. Preferably, the acid is poured into a container containing the polymer in a small amount at a time with intermittent agitation. The volume increases, preferably doubles, after curing. This mixture tends to form a sticky solid.

Alkylation processes contemplated in the present invention are those liquid based processes wherein mono- and iso-olefin hydrocarbons such as propene, butenes, pentenes, hexenes, heptenes, octenes, and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propene, butenes, pentenes, and mixtures thereof. More preferably, the olefin is isobutene. The alkylate hydrocarbon product comprises a major portion of highly branched high-octane aliphatic hydrocarbons having at least seven carbon atoms and less than 10 carbon atoms.

In order to improve selectivity of the alkylation reaction toward the production of the desirable highly branched aliphatic hydrocarbons having seven or more carbon atoms, a substantial stoichiometric excess of isoparaffin hydrocarbons is desirable in the reaction zone. Molar ratios of isoparaffin hydrocarbon to olefin hydrocarbons from about 2:1 to about 25:1 are contemplated in the present invention. Preferably, the molar ratio of isoparaffins to olefins will range from about 5 to about 20; and, most preferably, it will range from 8 to 15. It is emphasized, however, that the above recited ranges for the molar ratio of isoparaffins to olefin are those which have been found to be commercially practical operating ranges; but, generally, the greater the isoparaffins to olefin ratio in an alkylation reaction, the better the results in alkylate quality.

Isoparaffin and olefin reactant hydrocarbons normally employed in commercial alkylation processes are derived from refinery process streams and usually contain small amounts of impurities such as normal butane, propane, ethane, and the like. Such impurities are undesirable in large concentrations as they dilute reactants in the reaction zone, thus, decreasing reactor capacity available for the desired reactants and interfering with good contact of isoparaffins with olefin reactants. Additionally, in continuous alkylation processes wherein excess isoparaffin hydrocarbons are recovered from an alkylation reaction effluent and recycled for contact with additional olefin hydrocarbon, such non-reactive normal paraffin impurities tend to accumulate in the alkylation system. Consequently, process charged streams and/or recycle streams which contain substantial amounts of normal paraffin impurities are usually fractionated to remove such impurities and maintain their concentration at a low level, preferably less than about 5 volume % in the alkylation process.

Alkylation reaction temperatures within the contemplation of the present invention are in the range of from about 5° C. to about 150° C. Lower temperatures favor alkylation reaction of isoparaffins with olefins over competing olefin side reactions such as polymerization. However, overall reaction rates decrease with decreasing temperatures. Temperatures within the given range, and preferably in the range of from about 30° C. to about 130° C., provide good selectivity for alkylation of isoparaffins with olefins at commercially attractive reaction rates.

Reaction pressures contemplated in the present invention may range from pressures sufficient to maintain reactants in the liquid phase to about 15 atmospheres of pressure. Reactant hydrocarbons may be normally gaseous at alkylation reaction temperatures, thus, reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst composition of the present invention generally should be sufficient to provide for essentially complete conversion of olefin reactants in the alkylation zone. Preferably, the contact time is in the range of from about 0.05 minute to about 60 minutes. In the alkylation process of the present invention, employing isoparaffins to olefin molar ratios in the range of about 2:1 to about 25:1, wherein the alkylation reaction mixture comprises about 40 to 90 volume percent catalyst phase and about 10 to 60 volume percent hydrocarbon phase, and wherein good contact of olefins with isoparaffins is maintained in the reaction zone, essentially complete conversion of olefins may be obtained at olefin space velocities in the range of about 0.1 to about 200 volumes olefin per volume catalyst per hour (v/v/hr.) Optimum space velocities will depend upon the type of isoparaffins and olefin reactants utilized, the particular compositions of alkylation catalyst, and the alkylation reaction conditions. Consequently, the preferred contact times are sufficient for providing an olefin space velocity in the range of about 0.1 to about 200 v/v/hr. and allowing essentially complete conversion of the olefin reactant in the alkylation zone.

The process may be carried out either as a batch or continuous type of operation, although, it is preferred for economic reasons to carry out the process continuously. It has been generally established that in alkylation processes, the more intimate the contact between the feedstock and catalyst, the better the quality of alkylate product obtained. With this in mind, the present process, when operated as a batch operation, is characterized by the use of vigorous mechanical stirring or shaking of the reactants and catalysts.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence or other general means in the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

The following example demonstrates the advantages of the present invention. This example is by way of illustration only, and is not intended as a limitation upon the invention as set out in the appended claims.

EXAMPLE

A 62.46-gram quantity of trifluoromethane sulfonic acid (triflic acid) was mixed with 15.94 grams of polyacrylic acid. The acid was added in small amounts with intermittent agitation. The mixture was stirred, and after about 10 minutes, the volume of the mixture essentially doubled. The mixture became very thick, ultimately giving the appearance of a sticky or tacky solid, but was easily pourable.

A 15.40 gram quantity of the above composition was charged to a tubular reactor, with an inert support above and below the composition. The reactor temperature was set at 40° C. A feed comprising isobutane and isobutene (in a 12:1 weight ratio isobutane to isobutene) was introduced at 40 mL/hour (LHSV=2). After 3 hours, the feed rate was doubled (LHSV=4). Results are given below in Table I (components given on a $C_5^+$ weight percent basis).

TABLE I

Results of Alkylation Process using Trifluoromethanesulfonic Acid on a Polyacrylic Acid Support

| Parameter of Component | 2 hours | 3 hours | 4 hours |
| --- | --- | --- | --- |
| LHSV, hr−1 | 2 | 2 | 4 |
| Rx Temp, ° C. | 44.4 | 46.9 | 50.2 |
| C5 (wt. %) | 13.5 | 12.7 | 13.2 |
| C6 (wt. %) | 9.73 | 8.92 | 8.89 |
| C7 (wt. %) | 7.72 | 7.94 | 7.45 |
| C8 (wt. %) | 31.0 | 33.8 | 30.5 |
| C9+ (wt. %) | 32.5 | 36.5 | 39.9 |
| TMP (wt. %) | 22.4 | 23.3 | 20.9 |
| DMH (wt. %) | 9.91 | 10.4 | 9.37 |
| Estimated RON (gc) | 88.9 | 88.9 | 89.1 |
| Estimated T90, ° F. (gc) | 333 | 339 | 349 |

The T90 value is the temperature at which 90% of the sample would boil overhead. This is estimated by chromatographic analyses and regressions based on standard gas chromatography compositions.

The RON (research octane number) is determined by multiplying the octane number of each component by the component's mole fraction, and then taking the sum.

The data in Table I demonstrates that isobutane can be alkylated with isobutene using the inventive composition. The product is rich in trimethyl pentane (TMP) in relation to dimethyl hexane (DMH). Generally, the higher the TMP to DMH ratio, the higher the octane is in the alkylate product.

While this invention has been described in terms of the presently preferred embodiment, reasonable variations and modifications are possible by those skilled in the art. Such variations and modifications are within the scope of the described invention in the appended claims.

That which is claimed:

1. A pourable composition consisting of:
   a) an acid component selected from the group consisting of 1) a sulfuric acid, 2) a fluorosulfonic acid, 3) a perhaloalkylsulfonic acid, 4) an ionic liquid, 5) mixtures of Bronsted acids and Lewis acids, and 6) combinations of any two or more thereof; and
   b) a polymer holding the acid component in place in the composition, wherein said acid component is present in said composition in a range of from about 5 weight percent to about 90 weight percent based on the total weight of said composition.

2. A composition in accordance with claim 1 wherein said polymer is a polyacrylate having a formula of [—CH$_2$—CH(CO$_2$R)—]$_n$ where R is a Group IA element.

3. A composition in accordance with claim 2, wherein said Group IA element is hydrogen.

4. A composition in accordance with claim 1 wherein said acid component is trifluoromethanesulfonic acid.

5. A composition in accordance with claim 1 wherein said ionic liquid comprises a cation and an anion; wherein said cation is selected from the group consisting of ions defined by the formulas:

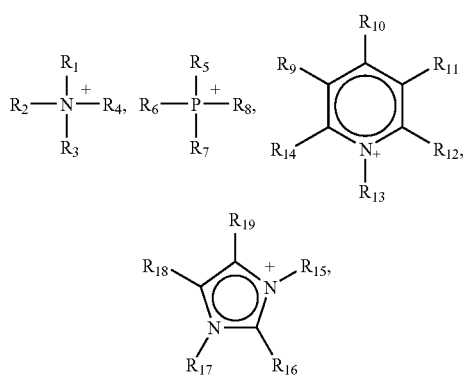

and combinations of any two or more thereof, wherein:
   $R_1$, $R_2$, $R_3$, $R_5$, $R_6$ and $R_7$ are selected from saturated and unsaturated hydrocarbons containing from 1 to 7 carbon atoms per molecule;
   $R_4$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ are selected from saturated and unsaturated hydrocarbons containing from 1 to 7 carbon atoms per molecule, and hydrogen; and
   wherein said anion is selected from the group consisting of halides of:
   Group IIIA metals, copper, zinc, iron and phosphorus.

6. A composition in accordance with claim 1 wherein said mixtures of Bronsted acids and Lewis acids comprise a Bronsted acid selected from the group consisting of hydrofluoric acid, sulfuric acid, trifluoromethane sulfonic acid, and combinations of any two or more thereof.

7. A composition in accordance with claim 1 wherein said acid component is present in said composition in a range of from about 30 weight percent to about 85 weight percent based on the total weight of said composition.

8. A composition in accordance with claim 1 wherein said acid component is present in said composition in a range of from about 50 weight percent to about 80 weight percent based on the total weight of said composition.

* * * * *